United States Patent
Murooka et al.

(10) Patent No.: US 8,184,292 B2
(45) Date of Patent: May 22, 2012

(54) UNEVENNESS DETECTING APPARATUS, METHOD, AND COMPUTER READABLE MEDIUM

(75) Inventors: Takashi Murooka, Kanagawa (JP); Hideyasu Ishibashi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 294 days.

(21) Appl. No.: 12/569,814

(22) Filed: Sep. 29, 2009

(65) Prior Publication Data
US 2010/0079757 A1  Apr. 1, 2010

(30) Foreign Application Priority Data
Sep. 30, 2008 (JP) ................ 2008-255585

(51) Int. Cl.
*G01J 4/00* (2006.01)
(52) U.S. Cl. ..... 356/369; 356/364; 356/365; 356/237.1; 356/239.7
(58) Field of Classification Search .......... 356/364–369, 356/237.1, 237.2, 239.7
See application file for complete search history.

(56) References Cited

U.S. PATENT DOCUMENTS

| | | | | |
|---|---|---|---|---|
| 4,547,073 A | * | 10/1985 | Kugimiya | 356/613 |
| 5,016,009 A | * | 5/1991 | Whiting et al. | 341/67 |
| 5,225,890 A | * | 7/1993 | Lee et al. | 356/613 |

FOREIGN PATENT DOCUMENTS

| | | | |
|---|---|---|---|
| JP | 408285556 A | * | 11/1996 |
| JP | 10-165357 | | 6/1998 |
| JP | 02006189505 A | * | 7/2006 |

* cited by examiner

*Primary Examiner* — Layla Lauchman
(74) *Attorney, Agent, or Firm* — McGinn IP Law Group, PLLC

(57) ABSTRACT

Provided is an unevenness detecting apparatus comprising a determining section that determines a polarization state of returned light obtained from radiated light; an uneven portion judging section that judges whether an uneven portion is present based on the polarization state determined by the determining section; a convex/concave identifying section that identifies whether the uneven portion is convex or concave based on image data, captured by an image capturing element, of the uneven portion; and an output section that outputs information identifying whether the uneven portion is convex or concave.

20 Claims, 6 Drawing Sheets

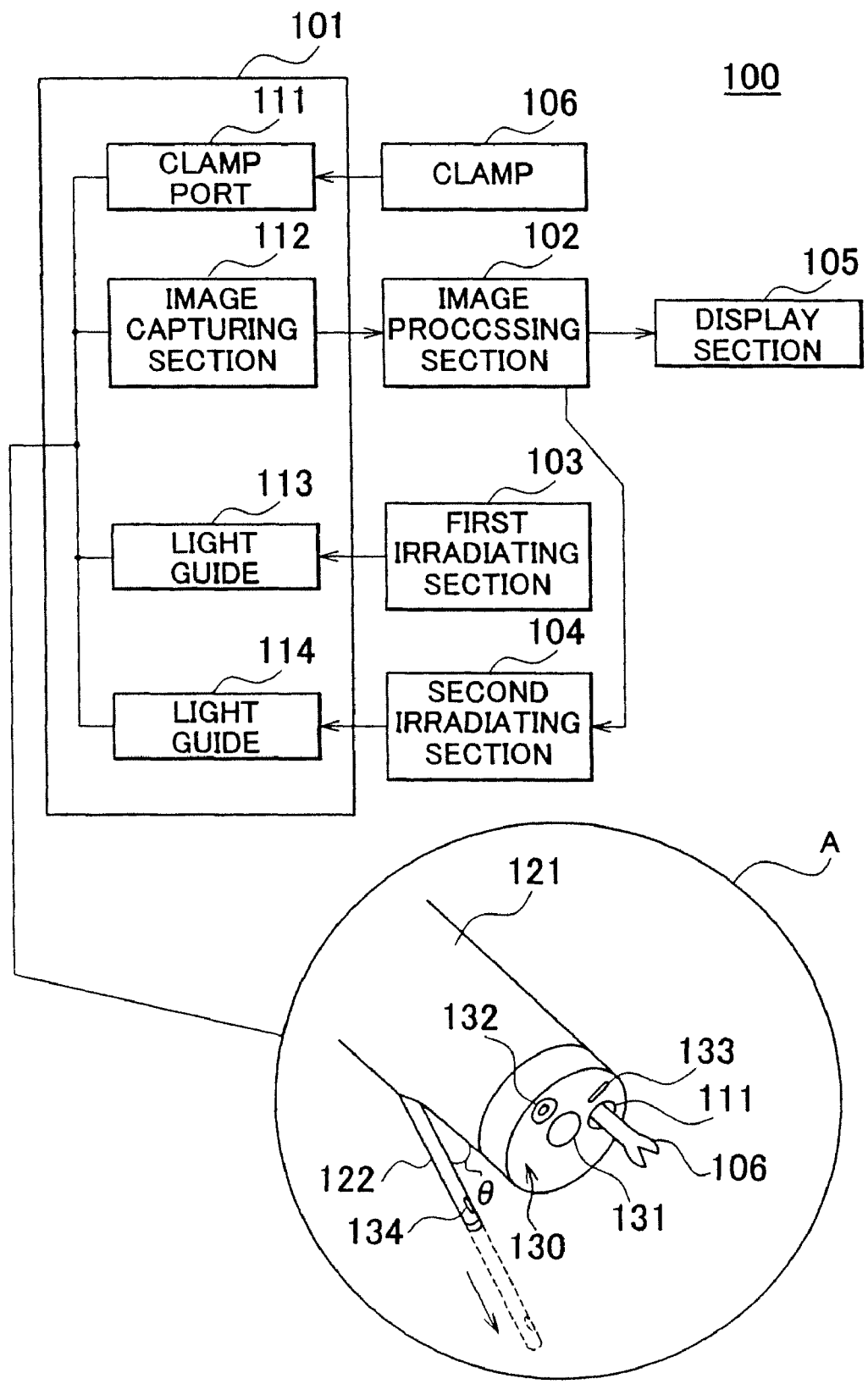
F I G. 1

UNEVENNESS DETECTING APPARATUS, METHOD, AND COMPUTER READABLE MEDIUM

The present application claims priority from a Japanese Patent Application No. 2008-255585 filed on Sep. 30, 2008.

BACKGROUND

1. Technical Field

The present invention relates to an unevenness detecting apparatus, a method, and a computer readable medium.

2. Related Art

Japanese Patent Application Publication No. 10-165357 discloses a technique for enabling a user to judge whether an uneven portion is present by shadows generated from light emitted to be diagonally incident to the uneven portion.

With the technology disclosed in JP 10-165357, a judgment as to the degree of unevenness and a judgment as to which portions are convex or concave are made by a user based on shadows, and so there is a concern that an uneven portion might go unnoticed if the user has poor judging ability.

SUMMARY

Therefore, it is an object of an aspect of the innovations herein to provide an unevenness detecting apparatus, a method, and a computer readable medium, which is capable of overcoming the above drawbacks accompanying the related art. The above and other objects can be achieved by combinations described in the independent claims. The dependent claims define further advantageous and exemplary combinations of the innovations herein.

According to a first aspect related to the innovations herein, one exemplary unevenness detecting apparatus may comprise a determining section that determines a polarization state of returned light obtained from radiated light; an uneven portion judging section that judges whether an uneven portion is present based on the polarization state determined by the determining section; a convex/concave identifying section that identifies whether the uneven portion is convex or concave based on image data, captured by an image capturing element, of the uneven portion; and an output section that outputs information identifying whether the uneven portion is convex or concave.

According to a second aspect related to the innovations herein, one exemplary method may include a method for judging presence of an uneven portion using a computer, comprising: determining a polarization state of returned light obtained from radiated light; judging whether the uneven portion is present based on the determined polarization state; identifying whether the uneven portion is convex or concave based on image data, captured by an image capturing element, of the uneven portion; and outputting information that identifies whether the uneven portion is convex or concave.

According to a second aspect related to the innovations herein, one exemplary computer readable medium may include a computer readable medium storing thereon a program that, when executed, causes a computer to function as a determining section that determines a polarization state of returned light obtained from radiated light; an uneven portion judging section that judges whether an uneven portion is present based on the polarization state determined by the determining section; a convex/concave identifying section that identifies whether the uneven portion is convex or concave based on image data, captured by an image capturing element, of the uneven portion; and an output section that outputs information identifying whether the uneven portion is convex or concave.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

BRIEF DESCRIPTION OF THE DRAWINGS

FIG. 1 shows an exemplary configuration of an unevenness detecting apparatus 100 according to an embodiment of the present invention.

DESCRIPTION OF EXEMPLARY EMBODIMENTS

Figure 2:
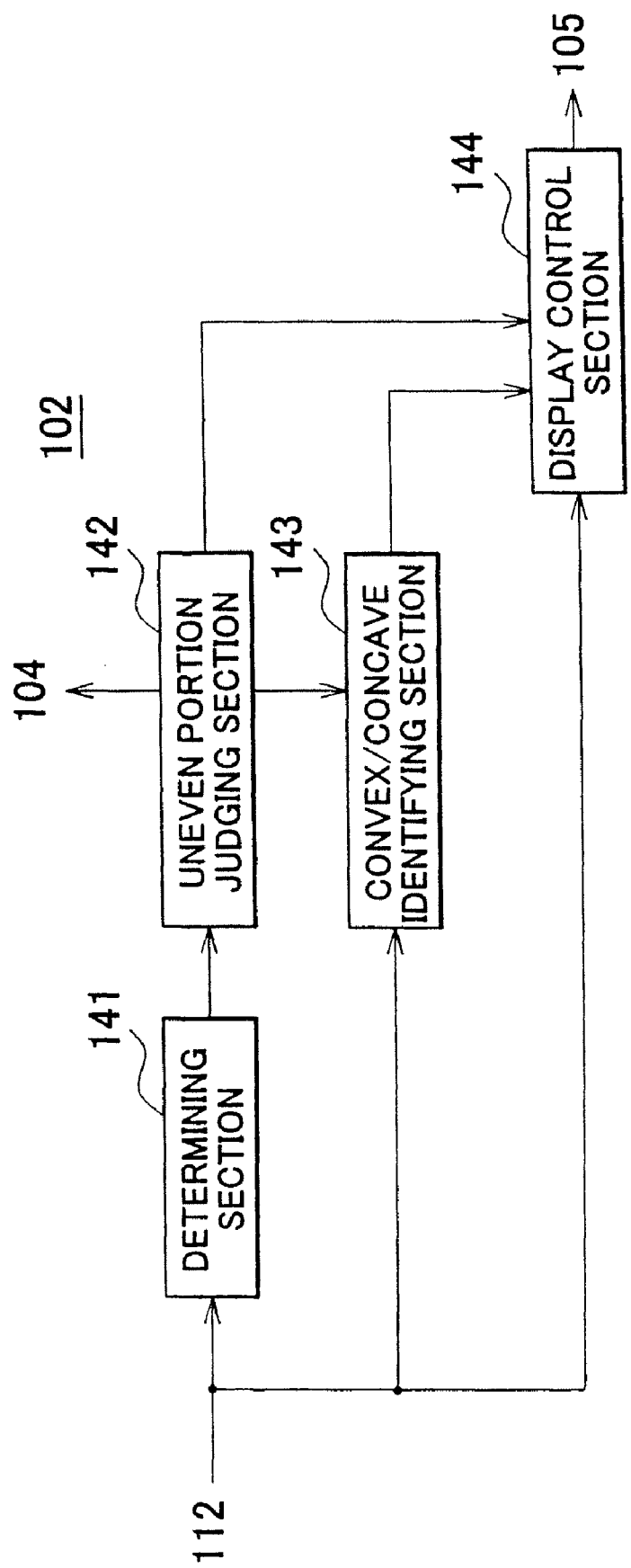
FIG. 2 shows an exemplary configuration of the image processing section 102.

Hereinafter, some embodiments of the present invention will be described. The embodiments do not limit the invention according to the claims, and all the combinations of the features described in the embodiments are not necessarily essential to means provided by aspects of the invention.

FIG. 1 shows an exemplary configuration of an unevenness detecting apparatus 100 according to an embodiment of the present invention. The unevenness detecting apparatus 100 is provided with an endoscope 101, an image processing section 102, a first irradiating section 103, a second irradiating section 104, and a display section 105. In FIG. 1, section "A" shows an enlarged view of a tip 121 of the endoscope 101.

The endoscope 101 includes a clamp port 111, an image capturing section 112, a light guide 113, and a light guide 114. The tip 121 of the endoscope 101 includes a lens 131 as a portion of the image capturing section 112 on a tip surface 130 thereof. The tip 121 includes an irradiation aperture 132 as a portion of the light guide 113 on the tip surface 130 thereof. The light guide 114 is a portion of the endoscope 101, and the tip of the light guide 114 is provided inside a separable section 122 that can be separated from the tip 121 of the endoscope 101.

One end of the separable section 122 is rotatably mounted on the tip 121 of the endoscope 101, and the other end of the separable section 122 has the irradiation aperture 134 as a portion of the light guide 114. The separable section 122 has the irradiation aperture 134 on a side surface thereof. The separable section 122 is provided with the irradiation aperture 134 such that light emitted from the second irradiating section 104 is radiated toward the tip 121 of the endoscope 101. The separable section 122 is usually in a closed state, that is, a state in which the angle between the separable section 122 and the tip 121 is 0 degrees. FIG. 1 shows an open angle between the separable section 122 and the tip 121. As shown by the dotted line in FIG. 1, the separable section 122 is extendable.

The first irradiating section 103 generates the light emitted from the tip 121 of the endoscope 101. The first irradiating section 103 includes a light source for generating the light. The light guide 113 may be made of optical fiber, for example. The light guide 113 guides the light emitted from the first irradiating section 103 to the tip 121 of the endoscope 101. The light generated by the first irradiating section 103 is emitted from the irradiation aperture 132. The first irradiating section 103 generates circularly polarized light. The light guide 113 maintains the polarized state of the light generated by the first irradiating section 103 to emit circularly polarized light from the irradiation aperture 132. Instead, the first irradiating section 103 may generate non-polarized light and a circular polarization filter that passes circularly polarized light may be provided to the irradiation aperture 132, so that the irradiation aperture 132 emits circularly polarized light. Here, unless explicitly stated otherwise, the first irradiating section 103 is assumed to emit light perpendicular to a subject, which is at an observed position.

The second irradiating section 104 generates the light emitted from the separable section 122 of the endoscope 101. The second irradiating section 104 includes a light source for generating the light. The light guide 114 may be made of optical fiber, for example. The light guide 114 guides the light emitted from the second irradiating section 104 to the separable section 122 of the endoscope 101. The light generated by the second irradiating section 104 is emitted from the irradiation aperture 134. The second irradiating section 104 controls the opening angle of the separable section 122. The second irradiating section 104 also controls the length of the separable section 122. More specifically, the separable section 122 includes a motor for changing the opening angle, and the second irradiating section 104 includes a motor control section for controlling this motor. Accordingly, this motor control section controls the opening angle. The separable section 122 has a structure that allows for length extension, and includes a motor for changing the length. The second irradiating section 104 includes a motor control section that controls this motor. The motor control section may be formed from an information processing apparatus such as a CPU. In this way, the second irradiating section 104 can irradiate the uneven portion with light that is diagonally incident thereto.

A clamp 106 is inserted into the clamp port 111, and the clamp port 111 guides the clamp 106 to the tip 121. The clamp 106 may be shaped as any type of tip. In addition to the clamp 106, various other tools for performing processes on an organism may be inserted into the clamp port 111. The nozzle 133 ejects water or air.

The image capturing section 112 includes an image capturing element and an optical system. The optical system includes the lens 131 and a polarizing section. The polarizing section includes a plurality of first polarization filters and second polarization filters, which linearly polarize light in directions orthogonal to each other. These first and second polarization filters are arranged in a lattice formation. The polarizing section may also include polarization filters with a polarization direction different from the linear polarization of the first and second polarization filters. The first and second polarization filters may be provided to correspond respectively to pixels in the image capturing element. In other words, the light passing through one polarization filter may be received by one pixel. The image capturing element captures an image based on the light passed by the polarizing section. The image capturing section 112 also includes an image capturing element driver for driving the image capturing element, an AD converter, and the like. The image data captured by the image capturing element is read by the image capturing element driver and converted into a digital signal by the AD converter.

The image capturing section 112 captures returned light, which is light emitted from the irradiation aperture 132 and/or the irradiation aperture 134 and reflected at the observed position. The image processing section 102 processes the image captured by the image capturing section 112. The image processing section 102 identifies a region of the uneven portion or the like in the captured image, and displays this region in the display section 105. The display section 105 includes a display, such as a liquid crystal display.

FIG. 2 shows an exemplary configuration of the image processing section 102. The image processing section 102 includes a determining section 141, an uneven portion judging section 142, a convex/concave identifying section 143, and a display control section 144. The determining section 141 determines the polarization state of the returned light resulting from the emitted circularly polarized light being returned. More specifically, the determining section 141 determines the polarization state based on a ratio between the amount of light passed by the first polarization filter and the amount of light passed by the second polarization filter. In other words, the determining section 141 determines the polarization state based on a ratio between (i) a charge amount of the light passed by the first polarization filter and captured by the image capturing element and (ii) a charge amount of the light passed by the second polarization filter and captured by the image capturing element. The determining section 141 determines the polarization state for the returned light from each of a plurality of regions.

Here, when the angle of incidence of the circularly polarized light relative to a flat surface is 90 degrees, the returned light becomes circularly polarized light. When the angle of incidence is not 90 degrees, the returned light becomes elliptically polarized light. The smaller the angle of incidence of the circularly polarized light to the flat surface, the greater the ellipticity of the elliptically polarized returned light. Accordingly, the polarization state of the returned light can be determined using the first and second polarization filters having polarization directions orthogonal to each other. For example, when the amount of light passed by the first polarization filter is equal to the amount of light passed by the second polarization filter, the polarization state of the returned light is circular. On the other hand, when the amount of light passed by the first polarization filter is not equal to the amount of light passed by the second polarization filter, the polarization state of the returned light is elliptical. The greater the difference between the amount of light passed by the first polarization filter and the amount of light passed by the second polarization filter, the greater the ellipticity of the elliptically polarized returned light.

The uneven portion judging section 142 judges whether there is an uneven portion based on the polarization state of the returned light determined by the determining section 141. The uneven portion judging section 142 may also judge whether a certain region has an uneven portion, based on the polarization state of the returned light from each region determined by the determining section 141. Since the polarization state of the returned light changes according to the inclination angle of the observed position relative to the incidence of the circularly polarized light, when circularly polarized light is perpendicularly incident to the observed position, an incline is judged to be present in a region from which the returned light is elliptically polarized, and so this region is judged to contain an uneven portion. Here, if the a region is judged to be uneven when the returned light differs only slightly from the circular polarization, there is a concern that substantially flat portions may be mistakenly judged to be uneven portions, and so a region is judged to be uneven only if the ellipticity for that region is greater than a set value. Here, an "uneven portion" refers to a portion with a depressed portion or with a protruding portion.

The uneven portion judging section 142 may store a table that associates polarization states with angles, and use this table to obtain the inclination angle of the observed position based on the polarization state determined by the determining section 141. Instead, the uneven portion judging section 142 may calculate the inclination angle of the observed position based on the determined polarization state. In this way, the uneven portion judging section 142 can obtain the inclination angle of the surface. The degree of unevenness of the uneven portion can be obtained from the polarization state of the returned light or the inclination angle of the observed position, and so, in the present embodiment, the polarization state of the returned light, the ellipticity of the polarization of the returned light, and the inclination angle of the observed position are all referred to as the degree of unevenness. The degree of unevenness represents the degree to which the surface protrudes or recedes. The uneven portion judging section 142 outputs, to the second irradiating section 104, the degree of unevenness of a region that is judged to be an uneven portion. The uneven portion judging section 142 outputs the region judged to be the uneven portion to the convex/concave identifying section 143 and the display control section 144.

The second irradiating section 104 irradiates the uneven portion with light at an angle according to the degree of unevenness of the uneven portion as judged by the uneven portion judging section 142. The angle according to the degree of unevenness is a relative measurement using the angle of incidence relative to a flat portion as a standard. In other words, the opening angle and length of the separable section 122 are controlled based on the unevenness of the region judged to be uneven by the uneven portion judging section 142, in order to diagonally irradiate this uneven portion with light. The second irradiating section 104 may store the table in which is recorded the length and opening angle corresponding to the degree of unevenness, and control the length and opening angle of the separable section 122 based on the degree of unevenness received from the uneven portion judging section 142. The second irradiating section 104 may instead calculate the length and opening angle of the separable section 122 based on the degree of unevenness received from the uneven portion judging section 142, and control the length and opening angle to be the calculated values. The image capturing section 112 captures an image based on the returned light resulting from the second irradiating section 104 diagonally radiating light to the portion judged to be uneven by the uneven portion judging section 142, and the captured image is then sent to the convex/concave identifying section 143. At this time, the image capturing may be performed with the polarizing section provided to the image capturing element being removed from the path of the light incident to the image capturing element. In this case, the polarizing section of the image capturing section 112 is configured to be able to move from the path of the light. In this way, non-polarized light is incident to the image capturing element.

The convex/concave identifying section 143 identifies whether the portion judged to be uneven by the uneven portion judging section 142 is convex or concave, based on the image captured when the second irradiating section 104 diagonally radiates light to the uneven portion. More specifically, the convex/concave identifying section 143 identifies whether the uneven portion is convex or concave based on a light-dark state of the uneven portion in the image. The convex/concave identifying section 143 can make this identification because the formation of shadows is different for a concave portion than for a convex portion when diagonally irradiated with light. The convex/concave identifying section 143 outputs the convex or concave identification to the display control section 144. The display control section 144 is one example of an output section that outputs information identifying whether the uneven portion is convex or concave. The output section may output the information identifying whether the uneven portion is convex or concave to the outside of the image processing section 102. The output section may output information identifying whether the uneven portion is convex or concave to the outside of the unevenness detecting apparatus 100. The output section may output a signal indicating whether the uneven portion is convex or concave.

The display control section 144 displays the image captured by the image capturing section 112 in the display section 105. If the uneven portion judging section 142 judges that there is an uneven portion, the display control section 144 may display the image such that the uneven portion is identifiable. In this way, a user can easily see where an uneven portion is. If the convex/concave identifying section 143 identifies the uneven portion as being convex or concave, the display control section 144 may display whether the identified uneven portion is convex or concave. In this way, the user can easily know whether the uneven portion is convex or concave.

Figure 3:
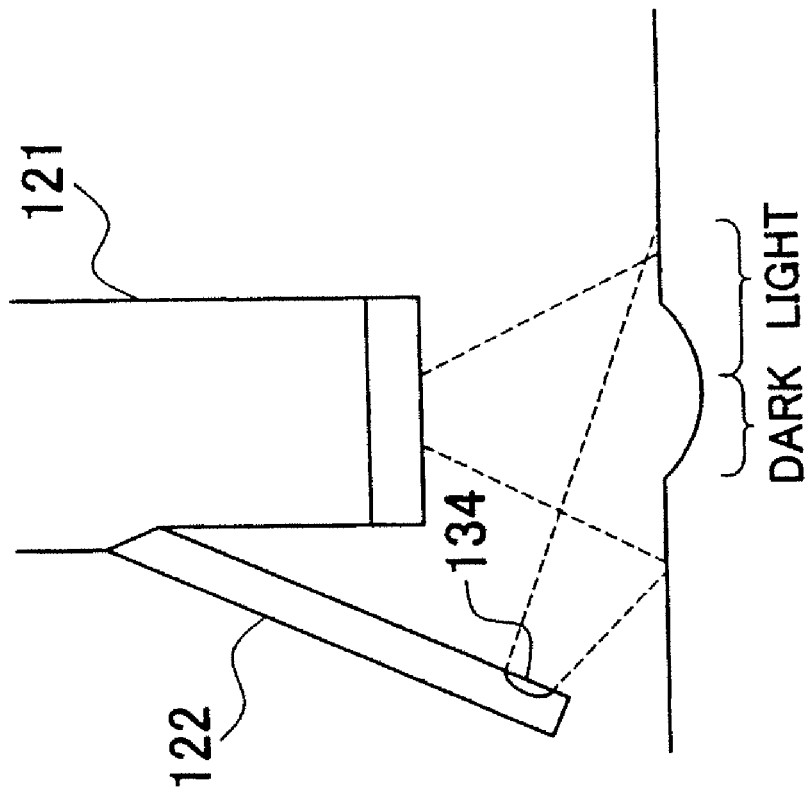
FIG. 3 shows examples of the light emitted from the unevenness detecting apparatus 100 and the light-dark state resulting from this emitted light.
Figure 3:
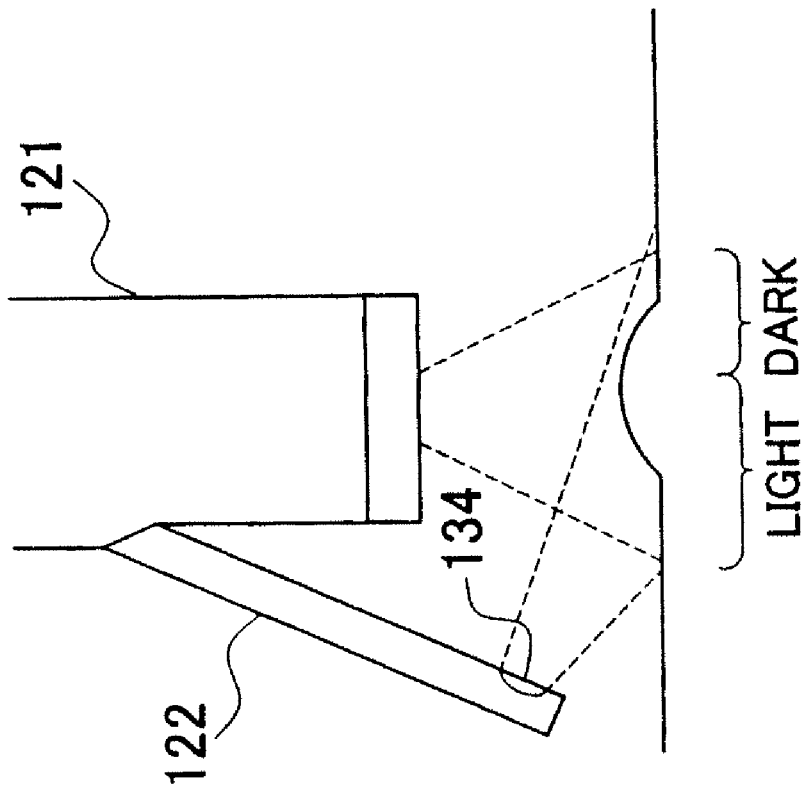

FIG. 3 shows examples of the light emitted from the unevenness detecting apparatus 100 and the light-dark state resulting from this emitted light. The drawing on the left side of FIG. 3 shows an exemplary light-dark state resulting from light radiated to an observed position that has a convex portion. The drawing on the right side of FIG. 3 shows an exemplary light-dark state resulting from light radiated to an observed position that has a concave portion. Here, the determining section 141 determines the polarization state of the returned light based on the image captured by the image capturing section 112 using the returned light obtained from circularly polarized light emitted by the first irradiating section 103. The uneven portion judging section 142 determines the polarization state of the returned light based on the image captured by the image capturing section 112 using the returned light determined by the determining section 141 to have circular polarization.

However, since the polarization state only changes depending on the angle of incidence of the light to the observed position, a judgment can be made based on the polarization state as to whether there is an uneven portion, but it cannot be ascertained whether this uneven portion is convex or concave. That is, by simply radiating circularly polarized light, the returned light for the convex portion and the returned light for the concave portion shown in FIG. 3 have the same polarization state, and both are therefore judged to have the same inclination angle. To solve this problem, the second irradiating section 104 radiates light diagonally to the portion judged to be uneven to create shadows, so that a judgment can be made as to whether the uneven portion is convex or concave based on the light and dark portions of the image.

The convex or concave identification may indicate a convex portion when a portion closer to the irradiation aperture 134 of the separable section 122 is light and a portion further from the irradiation aperture 134 is dark. The convex or concave identification may indicate a concave portion when a portion closer to the irradiation aperture 134 of the separable section 122 is dark and a portion further from the irradiation aperture 134 is light.

Depending on the form of the recess or protrusion in the uneven portion, it might be impossible to create shadows merely by radiating the light diagonally. For example, in the case of a very small recess or protrusion, shadows might not be formed if the light has an angle of incidence of approximately 45 degrees. As another example, in the case of a very large recess or protrusion, radiating the light to have an angle of incidence of approximately 25 degrees might result in the shadowy region being too large, which is unsuitable for the judgment. To solve this problem, the second irradiating section 104 changes the length and opening angle of the separable section 122 to diagonally radiate light at an angle according to the degree of unevenness of the portion judged to be uneven by the uneven portion judging section 142, so that an image with suitable light and dark portions can be obtained.

When the first irradiating section 103 radiates light and the image capturing section 112 captures the image used by the uneven portion judging section 142 to judge whether an uneven portion is present, the second irradiating section 104 need not radiate light. When the second irradiating section 104 radiates light and the image capturing section 112 captures the image used by the convex/concave identifying section 143 to judge whether the uneven portion is convex or concave, the first irradiating section 103 need not radiate light. When the image capturing section 112 captures the image used by the convex/concave identifying section 143 to judge whether the uneven portion is convex or concave, the first irradiating section 103 may radiate less light than the second irradiating section 104. As a result, it is easier to form shadows in the uneven portion.

After the convex/concave identifying section 143 judges whether the uneven portion is convex or concave, the second irradiating section 104 may stop radiating light. In this case, the first irradiating section 103 radiates light. Instead of stopping light radiation, the second irradiating section 104 may radiate less light than the first irradiating section 103. Causing the irradiating section 104 to radiate less or no light is beneficial because it prevents the shadows formed on the uneven portion from becoming too weak, which would cause precise observation to become more difficult. When the convex/concave identifying section 143 identifies whether the uneven portion is convex or concave, the first irradiating section 103 may radiate non-polarized light. As an example of a configuration for radiating polarized and non-polarized light, the light source in the first irradiating section 103 may be provided with a polarization filter that passes circularly polarized light. The polarizing filter may positioned in the path of the light emitted by the light source to generate circularly polarized light, and may be removed from the path of the light emitted by the light source to generate non-polarized light.

Figure 4:
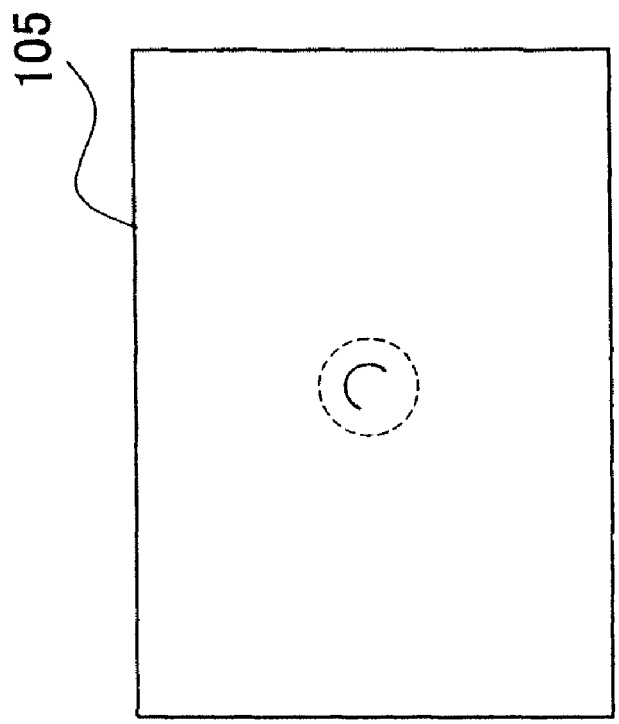
FIG. 4 shows an image displayed on the display section 105 at a certain time.
Figure 4:
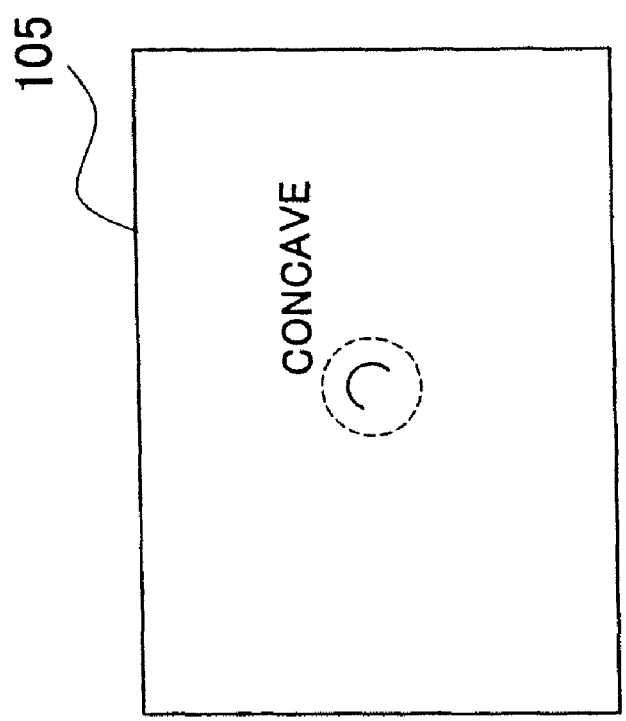

FIG. 4 shows images displayed on the display section 105 at certain times. The image shown on the right side of FIG. 4 is displayed later than the image shown on the left side. The image shown on the left side of FIG. 4 is displayed when the uneven portion judging section 142 judges there to be an uneven portion. The image shown on the right side of FIG. 4 is displayed when the convex/concave identifying section 143 identifies whether the uneven portion determined by the uneven portion judging section 142 is convex or concave. Here, the convex/concave identifying section 143 identifies the uneven portion to be concave.

As shown in FIG. 4, the uneven portion is displayed by encircling the region judged to contain the uneven portion with a dotted line. In this way, the user can easily see the location of the uneven portion. This uneven portion is identified by displaying a dotted line therearound, but may instead be identified by displaying a color or the like. As understood from the right side of FIG. 4, the convex/concave identifying section 143 displays the word "concave" near the uneven portion identified as being concave. In the same way, the convex/concave identifying section 143 displays the word "convex" near an uneven portion identified as being concave. Instead of using the words "convex" and "concave" to notify the user, marks and/or colors may be displayed to notify the user as to whether the uneven portion is convex or concave.

The display control section 144 may reproduce the shape of the uneven portion based on the angle of incidence at the uneven portion determined by the uneven portion judging section 142 and the convex/concave identification by the convex/concave identifying section 143, and display the reproduced shape in the display section 105. In this way, the user can see the shape of the uneven portion.

As described above, the present embodiment can easily determine whether an uneven portion is present based on the polarization of returned light obtained from radiated circularly polarized light. The present embodiment can easily identify whether the uneven portion is convex or concave based on shadows formed by diagonally radiating light on the uneven portion. The present embodiment can generate suitable shadows in the uneven portion by diagonally radiating the light at an angle corresponding to the unevenness of the uneven portion. The present invention enables a user to easily identify a region containing an uneven portion by displaying the uneven portion in an identifiable manner in the captured image. The present embodiment enables the user to easily identify whether the uneven portion is convex or concave by displaying information indicating whether the uneven portion is convex or concave. Each component described in the present embodiment, such as the image capturing section 112 and the like, may be controlled by a computer or an information processing apparatus such as a CPU or the like. The image processing section 102 may be realized as an electronic circuit, or may be realized as an information processing apparatus such as a CPU.

The embodiment described above may be modified in the following ways.

Figure 5:
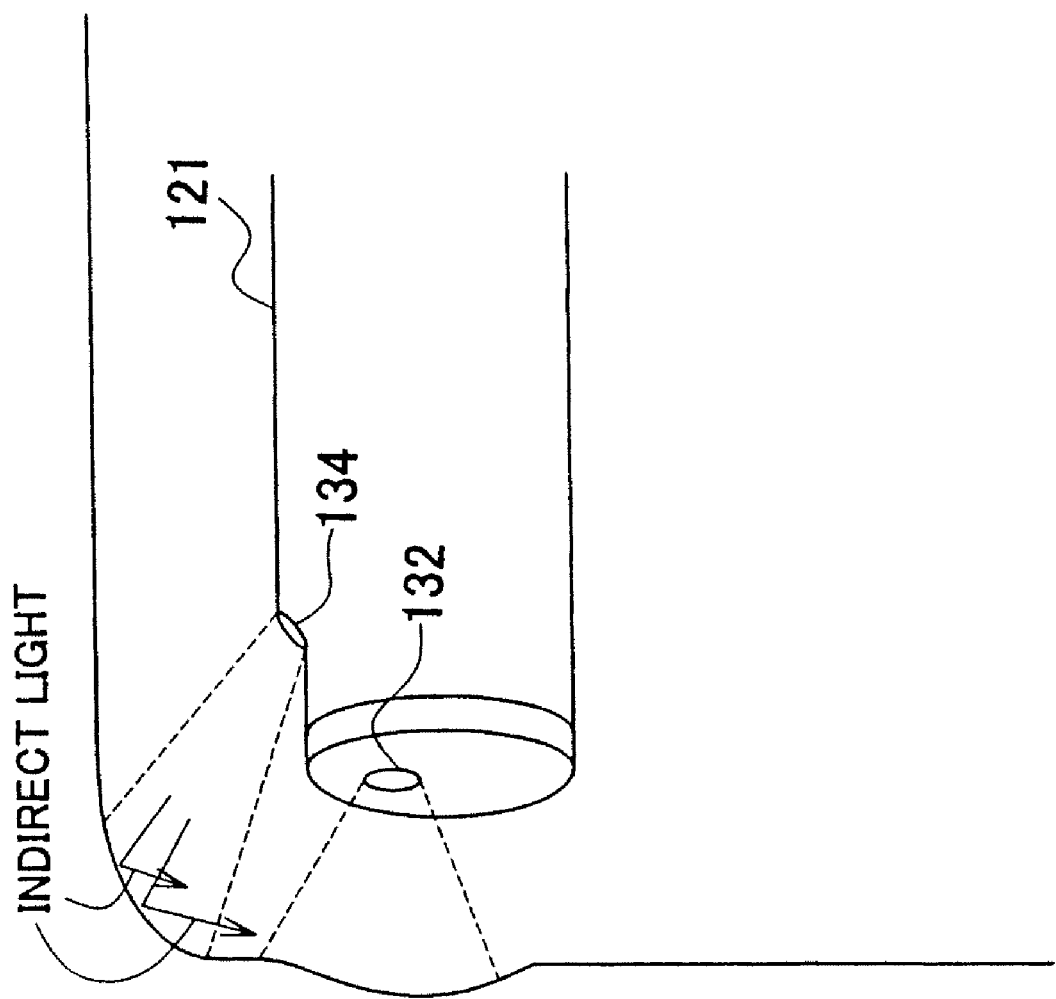
FIG. 5 shows an exemplary tip 121 of the endoscope 101 according to the first modification.

(1) In a first modification, light may be emitted from a side of the tip 121 of the endoscope 101, without providing the separable section 122. FIG. 5 shows an exemplary tip 121 of the endoscope 101 according to the first modification. The side of the tip 121 is provided with an irradiation aperture 134 that emits the light generated by the second irradiating section 104. The tip surface 130 of the tip 121 is provided with the irradiation aperture 132 that emits the light generated by the first irradiating section 103, in the same manner as the above embodiments. In FIG. 5, the lens 131, the clamp port 111 and the nozzle 133 are not shown. By providing the irradiation aperture 134 on the side of the tip 121, the light emitted from the irradiation aperture 134 directly hits a subject and is then reflected, and so the indirect light, which is light emitted by the second irradiating section 104 and reflected, diagonally irradiates an indirect position. In this way, shadows can be generated in the uneven portion using a simpler structure, which lowers the manufacturing cost.

Figure 6:
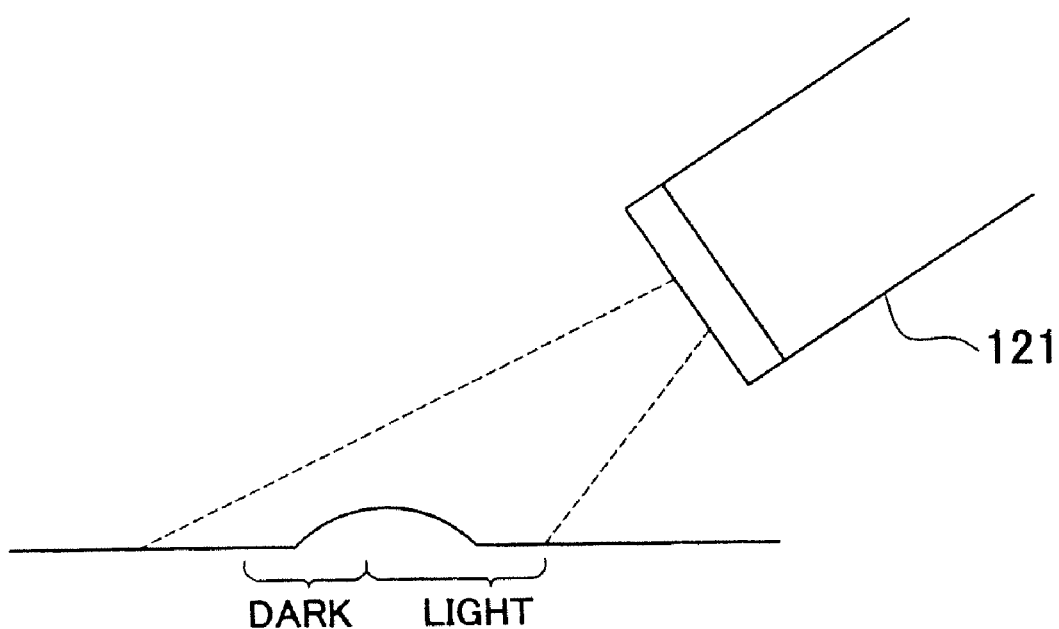
FIG. 6 shows an exemplary unevenness detecting method according to the second modification.
Figure 6:
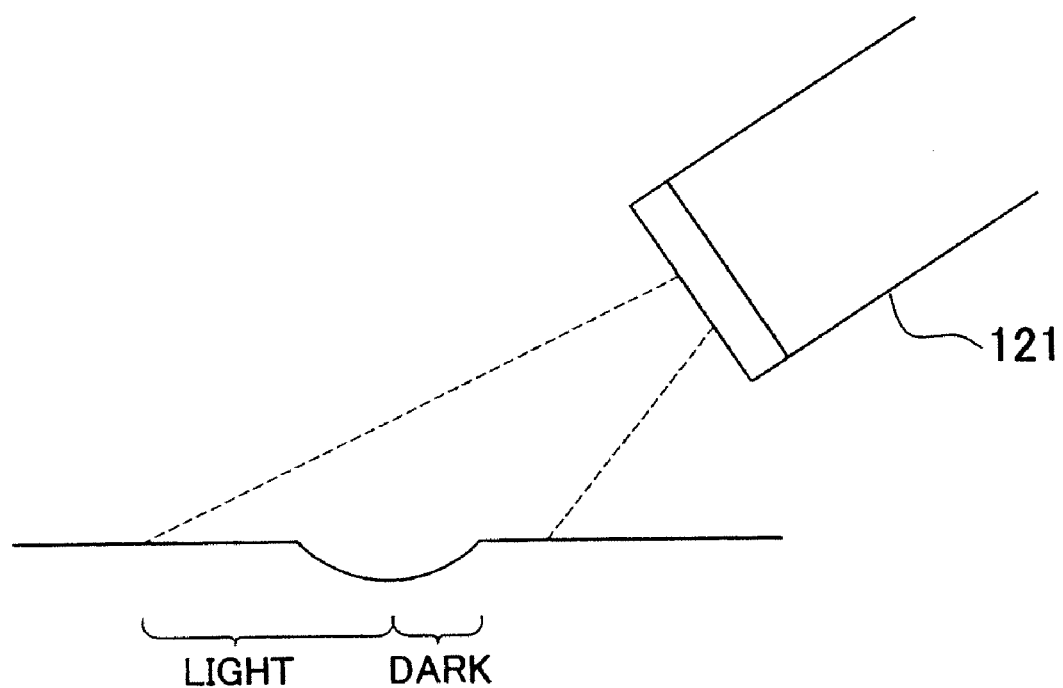

(2) A second modification is not provided with the separable section 122 or the second irradiating section 104. FIG. 6 shows an exemplary unevenness detecting method according to the second modification. As shown in FIG. 6, the tip 121 of the endoscope 101 is slanted relative to the observed position, so that the light emitted by the first irradiating section 103 is diagonally incident to the observed position. In this way, shadows can be generated on the uneven portion without providing the second irradiating section 104. Here, the first irradiating section 103 radiates light diagonally to the observed position, and so returned light from a flat portion of the observed position, that is, a portion that is not uneven, is circularly polarized. The uneven portion judging section 142 can judge the presence of an uneven portion in a region based on the polarization state of all of the returned light. In other words, the uneven portion judging section 142 can judge an uneven portion to be present in a region having a different polarization state based on the polarization state of all of the returned light.

More specifically, the second modification acquires the polarization state of the returned light from each region. A range over which regions are gathered having returned light with substantially identical polarization states is judged to be flat, and a region for which the polarization state of the returned light differs from that of the returned light from a flat region is judged to contain an uneven portion. Since the angle of incidence is known based on the polarization state of the returned light in each region, a region including the uneven portion may be determined based on the overall angle of incidence. In other words, a range over which regions are gathered having substantially identical angles of incidence may be judged to be flat, and a region for which the angle of incidence differs from that of the flat region may be judged to contain an uneven portion. The uneven portion can be identified as being convex or concave based on the light-dark state of the region determined to contain an uneven portion. For example, the uneven portion may be identified as convex when the region containing the uneven portion has a distribution that changes from light to dark, in the stated order, in a direction of the path of the diagonally radiated light. The uneven portion may be identified as concave when the region containing the uneven portion has a distribution that changes from dark to light, in the stated order, in a direction of the path of the diagonally radiated light. In this way, the second modification has a simpler configuration, resulting in lower manufacturing cost.

(3) A third modification addresses a problem that, when the area of the uneven portion irradiated with light by the second irradiating section 104 is small relative to the total area of the uneven portion, it is difficult to identify whether the uneven portion is convex or concave based on a single image captured using light irradiating a certain position. The third modification may move the irradiated position, capture a plurality of images at different irradiated positions, and use the plurality of images to identify whether the uneven portion is convex or concave. In other words, the irradiated position, which is the position in the observed position at which the second irradiating section 104 radiates light, is moved, and the convex/concave identification is then made based on the light-dark state in a plurality of images captured at different irradiated positions. When the area of the uneven portion irradiated with light by the first irradiating section 103 is small relative to the total area of the uneven portion, it is difficult to identify whether the uneven portion is convex or concave based on a single image captured using light irradiating a certain position. Therefore, the third modification moves the irradiated position and identifies whether the uneven portion is convex or concave based on a plurality of images captured at different irradiated positions.

(4) In the above embodiments, the first irradiating section 103 radiates circularly polarized light, but in a fourth modification, the first irradiating section 103 may radiate light with different polarization. In other words, the first irradiating section 103 may radiate any one type of light from among non-polarized light, elliptically polarized light, and linearly polarized light. The uneven portion judging section 142 may determine whether an uneven portion is present based on the polarization state of the returned light obtained from the light radiated by the first irradiating section 103. That is, the uneven portion judging section 142 may determine whether an uneven portion is present based on the polarization state of the returned light obtained from the non-polarized light, elliptically polarized light, or linearly polarized light radiated by the first irradiating section 103.

(5) A fifth modification may be a combination of the first and third modifications, or of the second and third modifications. The fifth modification may be a combination of (i) any one of the first through third modifications and (ii) the fourth modification.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. An unevenness detecting apparatus comprising:
a determining section that determines a polarization state of returned light obtained from radiated light;
an uneven portion judging section that judges whether an uneven portion is present based on the polarization state determined by the determining section;
a convex/concave identifying section that identifies whether the uneven portion is convex or concave based on image data, captured by an image capturing element, of the uneven portion; and
an output section that outputs information identifying whether the uneven portion is convex or concave.

2. The unevenness detecting apparatus according to claim 1, wherein
the convex/concave identifying section identifies whether the uneven portion is convex or concave based on a light-dark state of the uneven portion, the light-dark state determined using a plurality of pieces of the image data captured by the image capturing element.

3. The unevenness detecting apparatus according to claim 1, further comprising:
a first irradiating section that radiates polarized light; and
a second irradiating section that radiates light to be diagonal relative to a surface judged to have an uneven portion by the uneven portion judging section, wherein
the determining section determines the polarization state of returned light obtained from the polarized light radiated by the first irradiating section.

4. The unevenness detecting apparatus according to claim 3, wherein
the first irradiating section radiates circularly polarized light.

5. The unevenness detecting apparatus according to claim 3, wherein
the second irradiating section radiates light to the uneven portion at an angle corresponding to a degree of unevenness of the uneven portion.

6. The unevenness detecting apparatus according to claim 3, wherein
the second irradiating section indirectly radiates light on the uneven portion.

7. The unevenness detecting apparatus according to claim 1, further comprising an irradiating section that radiates polarized light, wherein
the irradiating section radiates light diagonally to a surface judged to have the uneven portion.

8. The unevenness detecting apparatus according to claim 7, wherein
the irradiating section radiates circularly polarized light.

9. The unevenness detecting apparatus according to claim 1, further comprising a first polarization filter and a second polarization filter, which linearly polarize light in directions orthogonal to each other, wherein
the determining section determines the polarization state of the returned light by calculating ellipticity based on a ratio between an amount of light passed by the first polarization filter and an amount of light passed by the second polarization filter.

10. The unevenness detecting apparatus according to claim 1, wherein
the output section includes a display control section that displays a region of the uneven portion in an identifiable manner, along with the image captured by the image capturing element.

11. The unevenness detecting apparatus according to claim 10, wherein
the display control section displays whether the uneven portion is convex or concave, along with the image captured by the image capturing element.

12. The unevenness detecting apparatus according to claim 2, further comprising:
a first irradiating section that radiates circularly polarized light; and
a second irradiating section that radiates light to be diagonal relative to a surface judged to have an uneven portion by the uneven portion judging section, wherein
the determining section determines ellipticity of the returned light as the polarization state of returned light.

13. A method for judging presence of an uneven portion using a computer, comprising:
determining a polarization state of returned light obtained from radiated light;
judging whether the uneven portion is present based on the determined polarization state;
identifying whether the uneven portion is convex or concave based on image data, captured by an image capturing element, of the uneven portion; and
outputting information that identifies whether the uneven portion is convex or concave.

14. The method according to claim 13, wherein
identifying whether the uneven portion is convex or concave is based on a light-dark state of the uneven portion, the light-dark state determined using a plurality of pieces of the image data captured by the image capturing element.

15. The method according to claim 13, further comprising:
radiating polarized light; and
radiating light to be diagonal relative to a surface judged to have the uneven portion, wherein
determining a polarization state includes determining the polarization state of returned light obtained from the radiated polarized light.

16. The method according to claim 15, wherein
radiating polarized light includes radiating circularly polarized light.

17. A non-transitory computer-readable storage medium containing computer instructions stored therein for executing a computer to function as:
a determining section that determines a polarization state of returned light obtained from radiated light;
an uneven portion judging section that judges whether an uneven portion is present based on the polarization state determined by the determining section;
a convex/concave identifying section that identifies whether the uneven portion is convex or concave based on image data, captured by an image capturing element, of the uneven portion; and
an output section that outputs information identifying whether the uneven portion is convex or concave.

18. The non-transitory computer-readable storage medium according to claim 17, wherein
the convex/concave identifying section identifies whether the uneven portion is convex or concave based on a light-dark state of the uneven portion, the light-dark state determined using a plurality of pieces of the image data captured by the image capturing element.

19. The non-transitory computer-readable storage medium according to claim 17, wherein
the program causes the computer to function as:
a first irradiating section that radiates polarized light; and
a second irradiating section that radiates light to be diagonal relative to a surface judged to have an uneven portion by the uneven portion judging section, wherein
the determining section determines the polarization state of returned light obtained from the polarized light radiated by the first irradiating section.

20. The non-transitory computer-readable storage medium according to claim 19, wherein
the first irradiating section radiates circularly polarized light.

* * * * *